(12) United States Patent
Kajihara et al.

(10) Patent No.: US 7,851,618 B2
(45) Date of Patent: Dec. 14, 2010

(54) AMINATED COMPLEX-TYPE SUGAR CHAIN DERIVATIVES AND PROCESS FOR THE PRODUCTION THEREOF

(75) Inventors: Yasuhiro Kajihara, Yokohama (JP); Kazuhiro Fukae, Tokushima (JP)

(73) Assignee: Otsuka Chemical Co., Ltd., Osaka (JP)

( * ) Notice: Subject to any disclaimer, the term of this patent is extended or adjusted under 35 U.S.C. 154(b) by 394 days.

(21) Appl. No.: 10/565,799

(22) PCT Filed: Jul. 27, 2004

(86) PCT No.: PCT/JP2004/011036
§ 371 (c)(1), (2), (4) Date: Jan. 25, 2006

(87) PCT Pub. No.: WO2005/010053
PCT Pub. Date: Feb. 3, 2005

(65) Prior Publication Data
US 2007/0060543 A1  Mar. 15, 2007

(30) Foreign Application Priority Data
Jul. 28, 2003  (JP) .............................. 2003-202594

(51) Int. Cl.
*C07H 5/04* (2006.01)
*C07H 1/00* (2006.01)
*C07K 2/00* (2006.01)
(52) U.S. Cl. .................. 536/29.1; 536/124; 530/322
(58) Field of Classification Search ............... 536/29.1; 530/322
See application file for complete search history.

(56) References Cited

U.S. PATENT DOCUMENTS 5,280,113 A * 1/1994 Rademacher et al. ...... 536/55.2
5,807,943 A * 9/1998 Lee et al. .................. 526/238.2

FOREIGN PATENT DOCUMENTS

EP  0 413 675 A2  2/1991
EP  0 538 230 A1  4/1993

OTHER PUBLICATIONS

Wright et al. Trends in Biotechnology, 1997, 15, p. 26-32.*
Tuzikov, Alexander B. et al., "Conversion of Complex Sialooligosaccharides into Polymeric Conjugates and Their Anti-Influenza Virus Inhibitory Potency", *Journal of Carbohydrate Chemistry*, vol. 19, No. 9, pp. 1191-1200, (2000).
Manger, I.D. et al., "Synthesis of 1-*N*-Glycyl β-Oligosaccharide Derivatives. Reactivity of Lens culinaris Lectin with a Fluorescent Labeled Streptavidin Pseudoglycoprotein and Immobilized Neoglycolipid", *Biochemistry*, vol. 31, No. 44, pp. 10733-10740, (1992).
Wong, Simon Y.C. et al., "Synthetic Glycosylation of Proteins Using *N*-(β-Saccharide) Iodoacetamides: Applications in Site-Specific Glycosylation and Solid-Phase Enzymic Oligosaccharide Synthesis", *Biochemical Journal*, vol. 300, No. 3, pp. 843-850, (1994).

* cited by examiner

*Primary Examiner*—Shaojia Anna Jiang
*Assistant Examiner*—Jonathan S Lau
(74) *Attorney, Agent, or Firm*—Myers Bigel Sibley & Sajovec, P.A.

(57) ABSTRACT

An aminated complex-type oligosaccharide derivative of the formula (1)

(1)

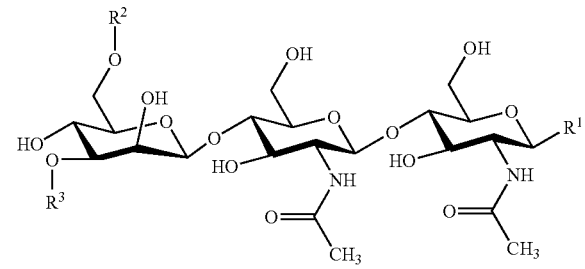

wherein $R^1$ is H—(CO)—CH$_2$X, —NH—(CO)—(CH$_2$)$_b$—CH$_2$X, isothiocyanate group, —NH—(CO)$_a$—(CH$_2$)$_b$—CO$_2$H or —NH—(CO)$_a$—(CH$_2$)$_b$—CHO, X being a halogen atom, a being 0 or 1, b being an integer of 1 to 4, $R^2$ and $R^3$ are a hydrogen atom or a group of the formulae (2) to (5) and may be the same or different, except for the case where both $R^2$ and $R^3$ are hydrogen or the formula (5), and the case where one of $R^2$ and $R^3$ is a hydrogen atom, with the formula (5) serving as the other thereof.

3 Claims, 3 Drawing Sheets

AMINATED COMPLEX-TYPE SUGAR CHAIN DERIVATIVES AND PROCESS FOR THE PRODUCTION THEREOF

This application is a 371 of international application PCT/JP2004/011036, which claims priority based on Japanese patent application No. 2003-202594 filed Jul. 28, 2003, which is incorporated herein by reference.

TECHNICAL FIELD

The present invention relates to 1-amino-complex-type asparagine-linked oligosaccharide derivatives (hereinafter referred to as "aminated complex-type oligosaccharide derivatives") and glycopeptides.

BACKGROUND ART

Figure 1:
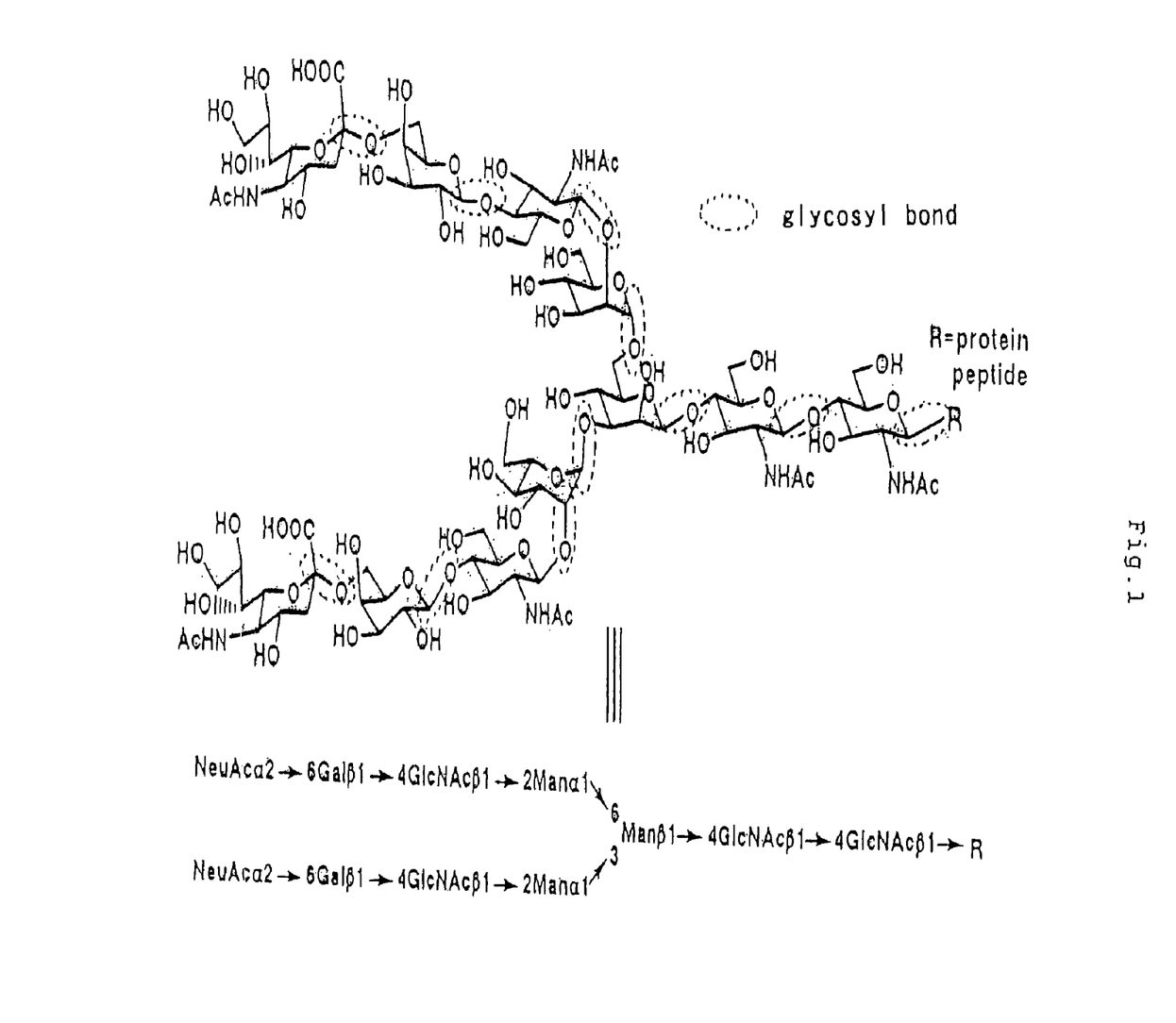
FIG. 1 is a diagram showing an example of an oligosaccharide structure.

Many of peptides (proteins) present in the living body have oligosacchrides. The term the "oligosaccharide" refers to a compound comprising monosaccharides which are linked to one another by a glycosyl bond in the form of a chain as shown in FIG. 1.

Figure 2:
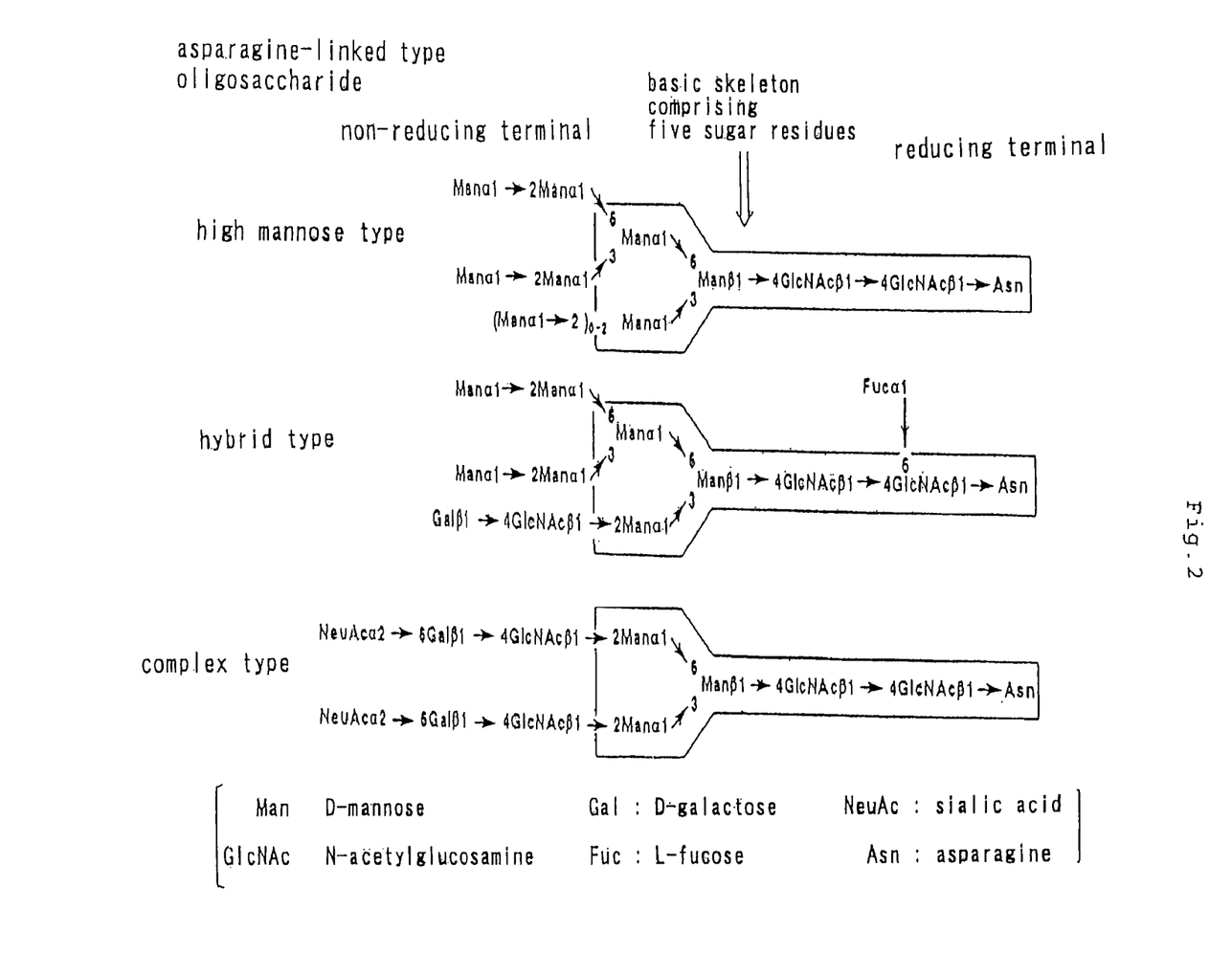
FIG. 2 is a diagram showing the classification of asparagine-linked oligosaccharides.

Oligosaccharides linked to a peptide (protein) are generally divided into two types according to the mode of linkage thereof to amino acids. These two types are asparagine-linked type (N-linked type) comprising an olgisaccharide linked to the side chain of asparagine (Asn), and the mucin-type (O-linked type) comprising an oligosaccharide linked to the side-chain hydroxyl group of serine (Ser) or threonine (Thr). All the asparagine-linked oligosaccharides have a basic skeleton comprising five sugar residues and are divided into the subgroups of the high mannose type, complex type and hybrid type according to the kind of the sugar residue at the non-reducing terminal of the oligosaccharide linked as shown in FIG. 2.

Such oligosaccharides are attached to a peptide (protein), covering the surface of the molecule thereof to thereby adjust the solubility of the peptide (protein), impart resistance to protease and retard metabolism in the blood, further acting to maintain the three-dimensional structure of the peptide (protein).

Typical of the above is a glycopeptide (glycoprotein) which is human erythropoietin (EPO). This glycopeptide (glycoprotein) has a complex-type asparagine-linked oligosaccharide, and is an erythroid differentiation hormone acting on erythroid precursor cells to promote the proliferation and differentiation thereof and thus having the function of maintaining the number of erythrocytes in peripheral blood.

Extensive research has been made on the correlation between the oligosaccharide structure on peptides (proteins) and physiological activity to find that EPO having no oligosaccharide bonded thereto exhibits physiological activity in vitro but fails to exhibit physiological activity in vivo.

Although research has been made not only on such glycopeptides (glycoproteins) but also on various peptides (proteins) for use as pharmaceuticals, a problem still remains to be solved in that peptide (protein) preparations are readily decomposed and metabolized in blood with a protease (peptidase), consequently failing to maintain a sufficient concentration in blood.

An object of the present invention is to provide an aminated complex-type oligosaccharide derivative which can be maintained at a sufficient concentration in blood and a glycopeptide.

DISCLOSURE OF THE INVENTION

The present invention provides the following.
1. An aminated complex-type oligosaccharide derivative.
2. An aminated complex-type oligosaccharide derivative of the formula (1)

(1)

wherein $R^1$ is H—(CO)—$CH_2$X, —NH—(CO)—$(CH_2)_b$—$CH_2$X, isothiocyanate group, —NH—$(CO)_a$—$(CH_2)_b$—$CO_2$H or —NH—$(CO)_a$—$(CH_2)_b$—CHO, X being a halogen atom, a being 0 or 1, b being an integer of 1 to 4, $R^2$ and $R^3$ are a hydrogen atom or a group of the formulae (2) to (5) and may be the same or different, except for the case where both $R^2$ and $R^3$ are hydrogen or the formula (5), and the case where one of $R^2$ and $R^3$ is a hydrogen atom, with the formula (5) serving as the other thereof.

(2)

(3)

(4)

(5)

3. An aminated complex-type oligosaccharide derivative of the above wherein $R^1$ is a —NH-halogenated acetyl group.

4. A glycopeptide comprising the above aminated complex-type oligosaccharide derivative of and a thiol group of an amino acid bonded thereto.

5. A process for preparing a glycopeptide characterized by bonding a thiol group of an amino acid to the above aminated complex-type oligosaccharide derivative.

6. A glycopeptide comprising the above aminated complex-type oligosaccharide derivative and a thiol group of an amino acid bonded thereto, the glycopeptide being an antibody.

7. A process for preparing a glycopeptide characterized by cleaving a saccharide of a glycopeptide from an amino acid and subsequently bonding the above aminated complex-type oligosaccharide derivative to the resulting peptide.

8. A glycopeptide prepared by cleaving a saccharide of a glycopeptide from an amino acid and subsequently bonding the above aminated complex-type oligosaccharide derivative to the resulting peptide, the glycopeptide prepared being an antibody.

The aminated complex-type oligosaccharide derivative of the present invention is a compound obtained by replacing the hydroxyl group attached to the carbon atom at the 1-position of a complex-type asparagine-linked oligosaccharide with one of —NH—(CO)—CH$_2$X, —NH—(CO)—(CH$_2$)$_b$—CH$_2$X, isothiocyanate group, —NH—(CO)$_a$—(CH$_2$)$_b$—CO$_2$H and —NH—(CO)$_a$—(CH$_2$)$_b$—CHO wherein X is a halogen atom, a is 0 or 1, and b is an integer of 1 to 4.

Examples of complex-type asparagine-linked oligosaccharides are those of the formula (6)

(6)

wherein $R^4$ and $R^5$ are each a hydrogen atom and a group of the formulae (2) to (5), and may be the same or different, except for the case where both $R^4$ and $R^5$ are hydrogen or the formula (5), and the case where one of $R^4$ and $R^5$ is a hydrogen atom, with the formula (5) serving as the other thereof.

The complex-type asparagine-linked oligosaccharide can be prepared, for example, according to WO 03/008431. Alternatively usable is a process for cleaving the oligosaccharide from a glycoprotein using an enzyme or chemically. The enzyme to be used is glycopeptidase A or N-glycanase. Hydrazine decomposition is usable for preparing the oligosaccharide by the chemical cleavage process.

The aminated complex-type oligosaccharide derivative of the present invention is a compound obtained by replacing the hydroxyl group attached to the carbon atom at the 1-position of a complex-type asparagine-linked oligosaccharide with one of —NH—(CO)—CH$_2$X, —NH—(CO)—(CH$_2$)$_b$—CH$_2$X, isothiocyanate group, —NH—(CO)$_a$—(CH$_2$)$_b$—CO$_2$H and —NH—(CO)$_a$—(CH$_2$)$_b$—CHO wherein X is a halogen atom, a is 0 or 1, and b is an integer of 1 to 4. The compound can be represented, for example, by the formula (1). The halogen atom mentioned is, for example, fluorine, chlorine, bromine or iodine atom.

(1)

In the above formula, $R^1$ to $R^3$ are the same as above.

The aminated complex-type oligosaccharide derivative can be prepared by a known process, for example, by reacting a compound having —NH—(CO)—(CH$_2$)$_b$—CH$_2$X, isothiocyanate group, —NH—(CO)$_a$—(CH$_2$)$_b$—CO$_2$H and —NH—(CO)$_a$—(CH$_2$)$_b$—CHO wherein X is a halogen atom, a is 0 or 1, and b is an integer of 1 to 4 with an aminated complex-type oligosaccharide derivative. More specifically, when $R^1$ is —NH-bromoacetyl group, the desired derivative can be obtained by reacting a 1-amino-complex-type asparagine-linked oligosaccharide with bromoacetic acid in a solvent in the presence of a condensation agent. The solvent to be used is one capable of dissolving 1-amino-complex-type asparagine-linked oligosaccharide and bromoacetic acid therein, such as water, DMF, etc. Examples of useful condensation agents are 1-mesitylenesulfonyl-3-nitro-1,2,4-triazole (MSNT), dicyclohexylcarbodiimide (DCC), diisopropylcarbodiimide (DIPCDI), etc. It is desirable to use 1 to 10 moles of the condensation agent per mole of the 1-amino-complex-type asparagine-linked oligosaccharide. It is also desirable to use 1 to 10 moles of bromoacetic acid per mole of the 1-amino-complex-type asparagine-linked oligosaccharide. The reaction is conducted usually at 0 to 80° C., preferably 10 to 60° C., more preferably 15 to 35° C., usually for 30 minutes to 5 hours. On completion of the reaction, the reaction mixture is purified by a suitable known method [e.g., by high performance liquid column chromatography (HPLC)].

The glycopeptide of the invention having a 1-amino-complex-type asparagine-linked oligosaccharide incorporated therein is a glycopeptide comprising a peptide composed of desired amino acids bonded to one another by a peptide linkage, and the 1-amino-complex-type asparagine-linked oligosaccharide bonded to the peptide at the thiol group of the peptide.

The term "peptide" as used herein refers to a compound formed from two or more amino acids of the same kind or different kinds by the combination of the carboxyl group of one of the acids with the amino group of another by an acid amide bond, namely, by a peptide linkage (—CO—NH—), upon dehydration. Relatively small compounds comprising up to about 10 amino acids are termed oligopeptides, and larger compounds of this type are termed polypeptides. Polypeptides includes proteins.

Peptides can be prepared by solid-phase synthesis, liquid-phase synthesis or synthesis from cells, or can be obtained as naturally occurring peptides as by separation or extraction.

The glycopeptide of the invention having a 1-amino-complex-type asparagine-linked oligosaccharide incorporated therein can be prepared by reacting an aminated complex-type oligosaccharide with a peptide having a thiol group. The reaction is conducted usually at 0 to 80° C., preferably at 10 to 60° C., more preferably at 15 to 35° C., usually for 30 minutes to 5 hours. After the completion of the reaction, the reaction mixture is purified suitably by a known method [for example, by high performance liquid column chromatography (HPLC)]. Stated more specifically, an aminated complex-type oligosaccharide is reacted with a peptide having a thiol group in a phosphate buffer at room temperature. After the completion of the reaction, the product is purified by HPLC, whereby a glycopeptide of the invention can be obtained which has a 1-amino-complex-type asparagine-linked oligosaccharide incorporated therein.

Furthermore, an aminated complex-type oligosaccharide derivative is reacted by the above process with a peptide-linked oligosaccharide having a thiol group which has a saccharide or an oligosaccharide bonded thereto in advance, whereby a glycopeptide can be obtained which has a 1-amino-complex-type asparagine-linked oligosaccharide incorporated therein and having a plurality of saccharides or oligosaccharides.

Furthermore, an aminated complex-type oligosaccharide derivative is reacted with a glycopeptide having a thiol group which has a saccharide or an oligosaccharide bonded thereto in advance, and the saccharide or oligosaccharide bonded in advance is cleaved, whereby a glycopeptide can be obtained which has a 1-amino-complex-type asparagine-linked oligosaccharide attached thereto. At this time, it is desired that the saccharide or oligosaccharide bonded in advance be cleaved, for example, using an enzyme. Although the cleavage may be effected before or after the aminated complex-type oligosaccharide derivative is introduced into the peptide, it is desirable to effect the cleavage simultaneously with the introduction of the derivative. The cleavage enzyme may be one useful for cleaving a saccharide or the reducing terminal of an oligosaccharide from a peptide (i.e., a sugar hydrolase). The enzyme to be used is, for example, PNGase F. The reaction is conducted usually at 0 to 80° C., preferably at 10 to 60° C., more preferably at 15 to 35° C., usually for 30 minutes to 5 hours. After the completion of the reaction, the reaction mixture is purified suitably by a known method [for example, by high performance liquid column chromatography (HPLC)].

The glycopeptide of the invention having a 1-amino-complex-type asparagine-linked oligosaccharide incorporated therein is superior to naturally occurring complex-type asparagine-linked glycopeptide in resistance to sugar hydrolase (less prone to hydrolysis). The glycopeptide of the invention therefore exhibits improved stability in blood and prolonged life therein.

The glycopeptide of the invention having an aminated complex-type oligosaccharide derivative incorporated therein is uniform in amino acid sequence of the peptide, the linkage position of the oligosaccharide, or structure or kind of oligosaccharide, so that when the glycopeptide is in the form of physiologically active molecules, (e.g., an antibody), the physiologically active molecules are uniform in physiological activity.

Using the process of the invention for preparing the glycopeptide having an aminated complex-type oligosaccharide derivative incorporated therein, the 1-amino complex-type oligosaccharide derivative can be selectively bonded to the thiol group of the peptide, and in other words the compextype asparagine-linked oligosaccharide can be selectively introduced into a desired position of the peptides.

Glycopeptide having a high molecular weight (for example, of at least 10,000) can be prepared by the process of the invention for preparing the glycopeptide having an aminated complex-type oligosaccharide derivative incorporated therein.

The process of the invention for preparing the glycopeptide having an aminated complex-type oligosaccharide derivative incorporated therein is adapted to introduce a desired complex-type asparagine-linked oligosaccharide into an optional position without collapsing the folding of the glycopeptide.

BEST MODE OF CARRYING OUT THE INVENTION

The present invention will be described below in greater detail with reference to Reference Examples and Examples, to which the invention is not limited.

REFERENCE EXAMPLE 1

Preparation of Asparagine-Linked disialooligosaccharide

A 500 mg quantity of roughly purified SGP (sialylglycopeptide) and 10 mg (319 μmols) of sodium azide were dissolved in 25 ml of tris-hydrochloric acid-calcium chloride buffer solution (0.05 mol/l of TRIZMA BASE, 0.01 mol/l of calcium chloride, pH=7.5). To the solution was added a solution of 50 mg of actinase E (protease, product of Kaken Seiyaku) in 5 ml of tris-hydrochloric acid-calcium chloride buffer solution, followed by standing at 37° C. The solution was freeze-dried 115 hours later. The residue was purified by gel filtration column chromatography twice, giving 252 mg of the desired asparagine-linked disialooligosaccharide.

$^1$H-NMR (30° C.) δ5.13(s, 1H, Man-4-H-1), 5.07(d, 1H, J=9.5 Hz, GlcNAc1-H-1), 4.95(s, 1H, Man-4-H-1), 4.77(s, 1H, Man3-H-1), 4.61(d, 1H, J=7.6 Hz, GlcNAc2-H-1), 4.60 (d, 2H, J=7.6 Hz, GlcNAc5, 5-H-1), 4.44(d, 2H, J=8.0 Hz, Gal6, 6-H-1), 4.25(bd, 1H, Man3-H-2), 4.20(bdd, 1H, Man-4-H-2), 4.12(bd, 1H, Man-4-H-2), 2.94(dd, 1H, J=4.5 Hz, 17.2 Hz, Asn-βCH), 2.85(dd, 1H, J=7.0 Hz, 17.2 Hz, Asn-βCH), 2.67, 2.66(dd, 2H, J=4.6 Hz, 12.4 Hz, NeuAc7, 7-H-$3_{eq}$), 2.07(s, 3H, Ac), 2.06(s, 6H, Ac×2), 2.02(s, 6H, Ac×2), 2.01(s, 3H, Ac), 1.71(dd, 2H, J=12.4 Hz, 12.4 Hz, NeuAc7, 7-H-$3_{ax}$)

REFERENCE EXAMPLE 2

Preparation of Asparagine-Linked disialooligosaccharide Wherein Amino Group Nitrogen of Asparagine is Protected with Fmoc Group An 80 mg quantity (0.034 mmol) of the asparagine-linked disialooligosaccharide obtained in Reference Example 1 was dissolved in a solution of 2.7 ml of distilled water and 4.1 ml of acetone, and to the solution were added 34.7 mg (0.103 mmol) of 9-fluorenylmethyl-N-succinimidyl carbonate (Fmoc-OSn) and 11.5 mg (0.137 mmol) of sodium hydrogencarbonate. The mixture was stirred at room temperature for 2 hours. After the completion of reaction was recognized by TLC, the resulting solution was concentrated in a vacuum to remove acetone. The residue was applied to a column (ODS column) filled with a silica gel having octadecylsilyl group attached thereto) for purification, affording 60.1 mg of the desired product, i.e., Fmoc-asparagine-linked disialooligosaccharide in a yield of 68%.

$^1$H-NMR (30° C.)

8.01(2H, d, J=7.5 Hz, Fmoc), 7.80(2H, d, J=7.5 Hz, Fmoc), 7.60(2H, dd, J=7.5 Hz, Fmoc), 7.53(2H, dd, J=7.5 Hz, Fmoc), 5.23(1H, s, Man4-$H_1$), 5.09(1H, d, J=9.4 Hz, GlcNAc1-$H_1$), 5.04(1H, s, Man-4-$H_1$), 4.86(1H, s, Man3-$H_1$), 4.70~4.66(m, GlcNAc2-$H_1$ GlcNAc5, 5-$H_1$), 4.54(2H, d, J=7.9 Hz, Gal6, 6-$H_1$), 4.44(1H, d, FmocCH), 4.34(1H, bd, Man3-$H_2$), 4.29, (1H, bd, Man-4-$H_2$), 4.20(1H, bd, Man-4-$H_2$), 2.77(2H, dd, NeuAc7, 7-$H_{3eq}$), 2.80(1H, bdd, Asn-βCH), 2.62(1H, bdd, Asn-βCH), 2.14(18H, s×6, -Ac), 1.80(2H, dd, NeuAc7, 7-$H_{3ax}$)

REFERENCE EXAMPLE 3

Preparation of HOOC-Arg-Glu-Glu-Gln-Tyr-Cys-Ser-Thr-Tyr-Arg-Val-NH₂

Into a solid-phase synthesis column was placed 370 mg of HMPA-PEGA resin, which was thoroughly washed with $CH_2Cl_2$ and DMF for reaction.

Fmoc-Arg(OtBu)-OH, 1-mesitylenesulfonyl-3-nitro-1,2,4-triazole (MSNT) and N-methylimidazole were dissolved in $CH_2Cl_2$, and the solution was stirred for 5 minutes and thereafter placed into the solid-phase synthesis column containing the resin, followed by stirring at room temperature for 3 hours. The resin was thereafter washed with methylene chloride, isopropanol and DMF and dried. The unreacted hydroxyl group on the solid phase was thereafter acetylated using a 20% DMF solution of acetic anhydride for 20 minutes for capping. The resin was washed with DMF and stirred along with a 20% piperidine/DMF solution for 20 minutes to remove the protective Fmoc group, whereby resin-Arg-NH₂ was obtained. The product was washed with DMF and dried.

The resulting resin, and glutamic acid (Glu), glutamic acid (Glu), glutamine (Gln), tyrosine (Tyr), cysteine (Cys), Serine (Ser), threonine (Thr), tyrosine (Tyr), arginine (Arg) and valine (Val) were similarly subjected to condensation, followed by removal of the protective Fmoc group to obtain resin-Arg-Glu-Glu-Gln-Tyr-Cys-Ser-Thr-Tyr-Arg-Val-NH₂).

Used as the amino acids of glutamic acid (Glu), glutamine (Gln), tyrosine (Tyr), cysteine (Cys), Serine (Ser), threonine (Thr), arginine (Arg) and valine (Val) were each Fmoc-AA-Opfp (AA=amino acid) wherein the carboxyl group was pfp-esterified, and 3,4-dihydro-4-oxo-1,2,3-benzotriazin-3-yl (Dhbt) was used for condensation. All condensation reactions were conducted in a DMF solution.

The resin was washed and thereafter stirred along with a 95% aqueous solution of TFA at room temperature for 3 hours to cut off the resin. The resin was filtered off. The reaction mixture was concentrated in a vacuum at room temperature, thereafter dissolved in water and freeze-dried.

REFERENCE EXAMPLE 4

Preparation of HOOC-Ser-Ser-Asn(disialooligo)-Cys-Leu-Leu-Ala-NH₂

Into a solid-phase synthesis column was placed 370 mg of HMPA-PEGA resin, which was thoroughly washed with $CH_2Cl_2$ and DMF for reaction.

Fmoc-Ser(OtBu)-OH, 1-mesitylenesulfonyl-3-nitro-1,2,4-triazole (MSNT) and N-methylimidazole were dissolved in $CH_2Cl_2$, and the solution was stirred for 5 minutes and thereafter placed into the solid-phase synthesis column containing the resin, followed by stirring at room temperature for 3 hours. The resin was thereafter washed with methylene chloride, isopropanol and DMF and dried. The unreacted hydroxyl group on the solid phase was thereafter acetylated using a 20% DMF solution of acetic anhydride for 20 minutes for capping. The resin was washed with DMF and stirred along with a 20% piperidine/DMF solution for 20 minutes to remove the protective Fmoc group, whereby resin-Ser-NH₂ was obtained. The product was washed with DMF and dried.

Next, Fmoc-Ser(OtBu)-OH was used with HOBt.H₂O and DIPCDI for condensation.

Subsequently, Fmoc-asparagine-linked disialooligosaccharide obtained in Reference Example 2 was dissolved in a 1:1 solvent mixture of DMSO and DMF, and the solution, HATU and DIPEA were stirred at room temperature for 24 hours for condensation. The resulting resin was washed with DMF and thereafter stirred along with 10% acetic anhydride/2-propanol:methanol for 20 minutes for capping. The resin was washed with 2-propanol and DMF, and thereafter stirred along with 20% piperidine/DMF for 20 minutes to remove the protective Fmoc group. The resin was washed with DMF.

The resulting resin, and cysteine (Cys), leucine (Leu), leucine (Leu) and alanine (Ala) were similarly subjected to condensation, followed by removal of the protective Fmoc group to obtain resin-Ser-Ser-Asn(disialooligo)-Cys-Leu-Leu-Ala-NH₂.

Used as the amino acids of cysteine (Cys), leucine (Leu) and alanine (Ala) were each Fmoc-AA-Opfp (AA=amino acid) wherein the carboxyl group was pfp-esterified, and 3,4-dihydro-4-oxo-1,2,3-benzotriazin-3-yl (Dhbt) was used for condensation. All condensation reactions were conducted in a DMF solution.

The resin was washed and thereafter stirred along with a 95% aqueous solution of TFA at room temperature for 3 hours to cut off the resin. The resin was filtered off. The reaction mixture was concentrated in a vacuum at room temperature, thereafter dissolved in water and freeze-dried. The resulting product was dissolved in an aqueous solution of sodium hydroxide having a pH of 11 to hydrolyze the benzyl ester, followed by neutralization with acetic acid. The product was purified by HPLC to obtain the desired product, i.e., HOOC-Ser-Ser-Asn(disialooligo)-Cys-Leu-Leu-Ala-NH₂. (YMC-Pack A-314S-5 ODS 300×6.0 mm, developing solvents 0.1% TFA aqueous solution, B: 0.1% TFA acetonitrile:water=90:10, gradient A 100% 0.60 ml/min→B 100% 0.60 ml/min 60 min).

REFERENCE EXAMPLE 5

Preparation of disialooligosaccharide

SGP (100 mg) was dissolved in 50 mM phosphate buffer, 7.0 in pH, and PNGase F (BioLabs Inc., 1 U) was added to the solution, followed by incubation at 37° C. for 24 hours. The completion of reaction was confirmed by TLC (IPA:1 M NH₄OAc=1:1), and the reaction mixture was thereafter lyophilized. The lyophilized product was purified by gel permeation column chromatography (Sephadex G25, 1.5 cm×30 cm, water, flow rate 1.0 ml/min.) to obtain 74 mg of disialooligosaccharide.

¹H-NMR (400 MHz, D₂O)

δ 5.28(bd, 1H, GlcNAc1-H-1a), 5.23(s, 1H, Man-4-H-1), 5.03(s, 1H, Man-4'-H-1), 4.86(s, 1H, Man3-H-1), 4.70(m, 3H, GlcNAc2,5,5'-H-1), 4.53(d, 2H, Gal, 6'-H-1), 4.34(bs, 1H, Man3-H-2), 4.28(bd, 1H, Man-4-H-2), 4.20(bd, 1H, Man4'-H-2), 2.76(bdd, 2H, NeuAc7,7'-H-3 eq), 2.17(s, 3H, Ac), 2.16(s, 6H, Ac×2), 2.13(s, 6H, Ac×3), 1.80(dd, 2H, NeuAc7,7'-H-3ax)

REFERENCE EXAMPLE 6

Amination

The disialooligosaccharide (10 mg) obtained in Reference Example 5 was dissolved in a saturated aqueous solution of ammonium hydrogencarbonate to prepare a solution having a concentration of 30 mM. The solution was reacted at room temperature and held saturated at all times. The reaction was continued for 7 days, and when the reaction was found to have been almost completed by TLC (IPA:1 M $NH_4OAc$=1:1), the reaction mixture was freeze-dried as it was. Freeze-drying was repeated 3 times to remove the ammonium hydrogencarbonate and obtain 9 mg of disialooligosaccharide as aminated in a crude state.

$^1$H-NMR (400 MHz, $D_2O$)

δ 5.22(s, 1H, Man-4-H-1), 5.03(s, 1H, Man-4'-H-1), 4.86 (s, 1H, Man3-H-1), 4.69(m, 3H, GlcNAc2,5,5'-H-1), 4.53(d, 2H, Gal6,6'-H-1), 4.34(bs, 1H, Man3-H-2), 4.28(bd, 1H, Man-4-H-2), 4.23(bd, 1H, GlcNAc1-H-1), 4.20(bd, 1H, Man41-H-2), 2.76(bdd, 2H, NeuAc7,7'-H-3 eq), 2.17(s, 3H, Ac), 2.16(s, 6H, Ac×2), 2.12(s, 6H, Ac×3), 1.80(dd, 2H, NeuAc7,7'-H-3ax)

EXAMPLE 1

Bromoacetylation

The aminated disialooligosaccharide (crude, 5 mg) obtained in Reference Example 6 was dissolved in 100 μl of water, and 2 mg of ammonium hydrogencarbonate was added to the solution. A solution of 6.2 mg of bromoacetic acid in DMF (100 μl) and 4.6 mg of DCC were added to the mixture, followed by reaction at room temperature. The completion of reaction was confirmed by TLC (IPA:1 M NH$_4$OAc=2:1) 1.5 hours later, the reaction mixture was neutralized with sodium hydrogencarbonate, filtered and concentrated in a vacuum. The concentrate was then purified by gel permeation column chromatography (Sephadex G25, 1.5 cm×30 cm, water, flow rate 1.0 ml/min.) to obtain 4 mg of bromoacetylated disialooligosaccharide in a yield of 77%.

$^1$H-NMR (400 MHz, D$_2$O)

δ 5.22(s, 1H, Man-4-H-1), 5.16(bd, 1H, GlcNAc1-H-1), 5.03(s, 1H, Man-4'-H-1), 4.86(s, 1H, Man3-H-1), 4.70(m, 3H, GlcNAc2,5,5'-H-1), 4.53(d, 2H, Gal6,6'-H-1), 4.34(bs, 1H, Man3-H-2), 4.28(bd, 1H, Man-4-H-2), 4.20(bd, 1H, Man-4'-H-2), 2.77(bdd, 2H, NeuAc7,7'-H-3 eq), 2.17(s, 3H, Ac), 2.15(s, 6H, Ac×2), 2.12(s, 6H, Ac×2), 2.10(s, 3H, Ac), 1.80(dd, 2H, NeuAc7,7'-H-3ax)

EXAMPLE 2

A 2 mg quantity of the bromoacetylated disialooligosaccharide obtained in Example 1 and 1.8 mg of the peptide chain (Arg-Glu-Glu-Gln-Tyr-Cys-Ser-Thr-Tyr-Arg-Val) prepared in Reference Example 3 were dissolved in 170 μl of 100 mM phosphate buffer, 7.0 in pH, and the solution was incubated at room temperature. Disappearance of the materials was confirmed by HPLC, whereupon the reaction mixture was directly purified by HPLC [column: Mightysil-GP (5 μm), 10 mm diam.×250 mm, gradient: 0.1% trifluoroacetic acid/water 100% to 0.1% trifluoroacetic acid acetonitrile/water=90/10 75%; 60 min. linear, flow rate 2.5 ml] to obtain 2 mg of peptide-linked disialooligosaccharide in a yield of 64%.

$^1$H-NMR (400 MHz, D$_2$O)

δ 7.18(4H, Ph), 6.89(4H, Ph), 5.22(s, 1H, Man-4-H-1), 5.14(bd, 1H, GlcNAc1-H-1), 5.04(s, 1H, Man-4'-H-1), 4.86 (s, 1H, Man3-H-1), 4.69-4.63(m, 5H, GlcNAc2,5,5'-H-1, Tyr-αH, Cys-αH), 4.55-4.52(m, 4H, Gal6,6'-H-1, Gln-αH, Ser-αH), 4.44-4.38(m, 4H, Glu-αH×2, Arg-Hα, Thr-αH), 4.34(bs, 1H, Man3-H-2), 4.28(m, 3H, Man-4-H-2, Thr-βH), 4.23(d, 1H, J=5.9 Hz, Val-αH), 4.20(bd, 1H, Man-4'-H-2), 4.15(1H, Arg-αH), 3.30, 3.25(each 2H, Arg-δCH$_2$), 3.14-2.99(6H, Cys-)βH, Tyr-βH×2), 2.76(bdd, 2H, NeuAc7,7'-H-3 eq), 2.57(2H, Gln-γCH$_2$), 2.49, 2.35(each 2H, Glu-γCH$_2$), 2.23-2.10(m, 3H, Val-βH, Gln-βH), 2.16(s, 3H, Ac), 2.15(s, 6H, Ac×2), 2.12(s, 6H, Ac×2), 2.10-1.98(m, 6H, Glu-βH×2, Arg-βH), 2.07(s, 3H, Ac), 1.92-1.57(m, 8H, NeuAc7, 7'-H-3ax, Arg-βH, Arg-γCH$_2$×2), 1.23(d, 3H, Thr-γCH$_3$), 1.04(d, 6H, Val-γCH$_3$)

EXAMPLE 3

Synthesis Using
1-bromoacetyl-disialoogligosaccharide)

A 1 mg quantity of the peptide-linked disialooligosaccharide prepared in Reference Example 4 and 1 mg of bromoacetylated disialooligosaccharide obtained in Example 1 were dissolved in 200 μl of 100 mM phosphate buffer, PNGase F (5 U) which is an enzyme for cleaving asparagine-linked oligosaccharide from asparagine was added to the solution, and the mixture was reacted at room temperature. The product was purified by HPLC to obtain the desired product, i.e., a peptide-linked disialooligosaccharide comprising cysteine and a disialooligosaccharide attached thereto. (YMC-Pack A-314 S-5 ODS 300×6.0 mm, developer solvents: 0.1% TFA aqueous solution B: 0.1% TFA acetonitrile:water=90:10 gradient A 100% 0.60 ml/min.→B 100% 0.60 ml/min 60 min.)

TEST EXAMPLE 1

Resistance to Sugar Hydrolase

A 1 mg quantity of the peptide-linked disialooligosaccharide obtained in Example 3 was dissolved in 200 μl of 100 mM phosphate buffer, PNGase F (5 U), which is an enzyme for cleaving asparagine from asparagine-linked oligosaccharides, was added to the solution, and the mixture was reacted at room temperature to measure the time taken for the cleavage of disialooligosaccharide from the peptide. The cleavage time was 6 hours.

A 1 mg quantity of the peptide-linked disialooligosaccharide obtained in Reference Example 4 was dissolved in 200 μl of 100 mM phosphate buffer, PNGase F (5 U), which is an enzyme for cleaving asparagine from asparagine-linked oligosaccharides, was added to the solution, and the mixture was reacted at room temperature to measure the time taken for the cleavage of disialooligosaccharide from the peptide. The cleavage time was 30 minutes.

These results indicate that the peptide-linked disialooligosaccharide of Example 4 is higher than the peptide-linked disialooligosaccharide of the naturally bonded type (Reference Example 4) in resistance to sugar hydrolase.

EXAMPLE 4

Figure 3:
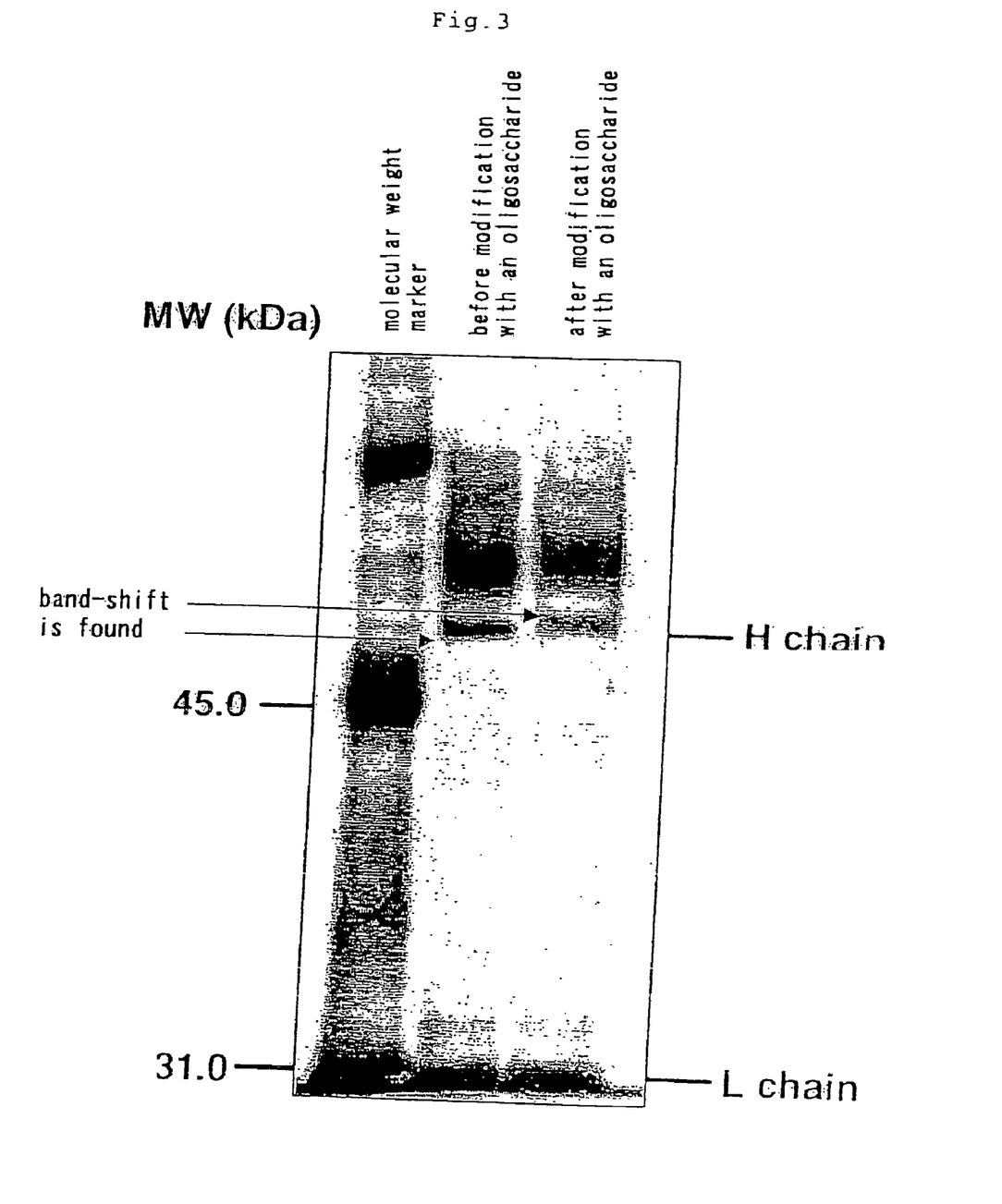
FIG. 3 is a diagram showing the electrophoresis of Anti-CD20 chimera antibody (mutant) and the same antibody as modified with an oligosaccharide.

A 43.9 μg quantity of Anti-CD20 chimera antibody (mutant) (product of Medical Biological Laboratories Co., Ltd., an antibody having an amino acid sequence wherein asparagine at the 297th position was replaced with cysteine by the mutation technique) and 100 μg of the bromoacetylated disialooligosaccharide of Example 1 were dissolved in 300 μl of 100 mM phosphate buffer, followed by incubation at room temperature. The reaction mixture obtained was purified by protein A column chromatography and gel permeation column chromatography to obtain an antibody comprising cysteine and disialooligosaccharide linked thereto. The antibody was identified by electrophoresis [10% SDS-PAGE (with 2-mercaptethanol), molecular weight marker: product of BIO-RAD, prestained SDS-PAGE standard broad range (Catalogue No. 161-0318)] and MASS. FIG. 3 shows the result.

INDUSTRIAL APPLICABILITY

The present invention provides a novel aminated complex-type oligosaccharide derivative which can be maintained at a sufficient concentration in blood, and a glycopeptide.

The invention claimed is:

1. A glycopeptide comprising an aminated complex-type oligosaccharide of the formula (1)

(1)

wherein $R^1$ is —NH—(CO)—$CH_2$X, X being a halogen atom, $R^2$ and $R^3$ are a hydrogen atom or a group of the formulae (2) to (5) and may be the same or different, except that $R^2$ and $R^3$ are not both hydrogen or the formula (5) at the same time and when one of R2 and R3 is hydrogen, the other is not the formula (5),

(2)

(3)

(4)

(5)

and the aminated complex-type oligosaccharide is bound to a thiol group of a peptide by displacement of halogen X of NH—(CO)—$CH_2$X further wherein the glycopeptide has about 12 times higher resistance to Peptide-N Glycosidase F (PNGase F) than the glycopeptide comprising said aminated complex-type oligosaccharide of formula (1), wherein R1 is an asparagine.

2. A glycopeptide as defined in claim 1 wherein the glycopeptide is an antibody.

3. A process for preparing a uniform glycopeptide composition comprising steps of (a) and (b) that are performed at the same time,
   (a) cleaving an asparagine-linked oligosaccharide of a glycopeptide from a peptide by Peptide-N Glycosidase F (PNGase F), wherein the resulting peptide has a thiol group, and (b) bonding an aminated complex-type oligosaccharide of the formula (1)

(1)

wherein $R^1$ is —NH—(CO)—CH$_2$X, X being a halogen atom, $R^2$ and $R^3$ are a hydrogen atom or a group of the formulae (2) to (5) and may be the same or different, except that $R^2$ and $R^3$ are not both hydrogen or the formula (5) at the same time and when on of R2 and R3 is hydrogen, the other is not the formula (5), (2)

to the thiol group of the resulting peptide by displacement of halogen X of —NH—(CO)—CH$_2$X.

* * * * *

UNITED STATES PATENT AND TRADEMARK OFFICE
CERTIFICATE OF CORRECTION

PATENT NO. : 7,851,618 B2  
APPLICATION NO. : 10/565799  
DATED : December 14, 2010  
INVENTOR(S) : Kajihara et al.

Page 1 of 1

It is certified that error appears in the above-identified patent and that said Letters Patent is hereby corrected as shown below:

On the Title Page, Item (75) Inventors:
    Please correct "Yasuhiro Kajihara, Yokohama (JP)"
        To read -- Yasuhiro Kajihara, Kanagawa (JP) --

On the Title Page, Item (73) Assignee:
    Please correct "Otsuka Chemical Co., Ltd., Osaka (JP)"
        To read -- Otsuka Chemical Co., Ltd., Osaka (JP); and
            Yasuhiro Kajihara, Kanagawa (JP) --

On the Title Page, Item (57) Abstract:
    Please correct "complex-type oligosaccharide derivative of the"
        To read -- complex-type oligosaccharide derivative, for example, of the --

In the Claims:
On Column 22, Claim 1, Line 54:
    Please correct "X of NH-(CO)-CH$_2$X further wherein"
        To read -- X of NH-(CO)-CH$_2$X, further wherein --

On Column 23, Claim 3, Line 21:
    Please correct "formula (5) at the same time and when on of R2"
        To read -- formula (5) at the same time and when one of R2 --

Signed and Sealed this  
Twenty-sixth Day of April, 2011

David J. Kappos  
*Director of the United States Patent and Trademark Office*